United States Patent [19]
Kim et al.

[11] Patent Number: 5,980,939
[45] Date of Patent: *Nov. 9, 1999

[54] CYCLOSPORIN-CONTAINING PHARMACEUTICAL COMPOSITION

[75] Inventors: Jung Woo Kim, Seoul; Hee Jong Shin, Kyunggi-do; Su Geon Yang, Seoul, all of Rep. of Korea

[73] Assignee: Chong Kun Dang Corp., Seoul, Rep. of Korea

[*] Notice: This patent issued on a continued prosecution application filed under 37 CFR 1.53(d), and is subject to the twenty year patent term provisions of 35 U.S.C. 154(a)(2).

[21] Appl. No.: 08/801,117

[22] Filed: Feb. 14, 1997

[30] Foreign Application Priority Data

Jul. 26, 1996 [KR] Rep. of Korea ................ 96-30726

[51] Int. Cl.$^6$ .................. A61K 9/10; A61K 9/48; A61K 47/24; A61K 47/34

[52] U.S. Cl. ............. 424/455; 514/937; 514/962; 514/975; 424/452

[58] Field of Search .................. 424/409, 452, 424/455, 456, 400, 439; 514/937, 962, 975

[56] References Cited

U.S. PATENT DOCUMENTS

| | | |
|---|---|---|
| 4,146,499 | 3/1979 | Rosano . |
| 4,388,307 | 6/1983 | Cavanak . |
| 5,342,625 | 8/1994 | Hauer et al. . |
| 5,543,393 | 8/1996 | Kim et al. . |

FOREIGN PATENT DOCUMENTS

| | | |
|---|---|---|
| 0 650 721 | 3/1995 | European Pat. Off. . |
| 95-2747 | 2/1995 | Rep. of Korea . |

OTHER PUBLICATIONS

CA 123: 266,72 Abstract of Japan Patent Document JP 07188046 AZ, Jul. 25, 1995.

Hee–Jong Shin et al, "Preparation and Bioequivalence Test of New Oral Solid Dosage Form of Cyclosporin A", Proceed. Intern. Symp. Control. Rel. Bioact. Mater., 23 (1996), Controlled Release Society, Inc., pp. 519–520.

(List continued on next page.)

*Primary Examiner*—Edward J. Webman
*Attorney, Agent, or Firm*—Oblon, Spivak, McClelland, Maier & Neustadt, P.C.

[57] ABSTRACT

The present invention relates to a pharmaceutical composition containing cyclosporin. More specifically, the present invention relates to a pharmaceutical composition containing cyclosporin, an oil component, a hydrophilic cosurfactant consisting of propylene carbonate or a mixture of propylene carbonate and polyoxyethylene-polyoxypropylene block copolymer, and a surfactant. The composition of the present invention is characterized in that it can be dissolved in an external phase such as water, artificial gastric juice and intestinal juice, etc. to form a self-emulsion with mild stirring and therefore, by appropriately adjusting the constitutional ratio of each component the diameter of particles in the inner phase of the emulsion thus formed can be readily controlled to 100 nm or below. The composition of the present invention can be formulated into the oral preparations such as soft capsules, hard capsules sealed with gelatin bending at the conjugated portion, oral liquid preparations, etc. When the composition of the present invention using propylene carbonate or its mixture with polyoxyethylene-polyoxypropylene block copolymer in a liquid state at room temperature is formulated into the soft capsule, it provides some advantages that it can inhibit the change in the capsule appearance and the precipitation of active ingredient due to the change in the solvent content, reduces the manufacturing cost to provide an economical effect and is substantially less toxic, in comparison to the soft capsule using ethanol, transcutol, propylene glycol, glycofurol, dimethylisosorbide, etc., in the prior art.

17 Claims, 4 Drawing Sheets

OTHER PUBLICATIONS

Chong–Kook Kim et al, "Preparation and Characterization of Cytarabine–Loaded w/o/w Multiple Emulsions", International Journal of Pharmaceutics, 124 (1995), pp. 61–67.

Zhong–Gao Gao et al, "Physicochemical Characterization and Evaluation of a Microemulsion System for Oral Delivery of Cyclosporin A", International Journal of Pharmaceuticals, 161 (1998), pp. 75–86.

Abstract No. 3217: Zhong–Gao Gao et al, "Pysiocochemical Characterization and Evaluation of Microemulsion System for Oral Delivery of Cyclosporin A", Pharmaceutical Research, AAPS, Nov. 1997 (Supplement), vol. 14, No. 11.

Abstract No. 3255; Hee–Jong Shin et al, "Preparation and Evaluation of Cyclosporin A Oral controlled Release Dosage Form Using Solid–State Microemulsion", AAPS Annual Meeting and Exposition, Bridging Gaps Within Drug Discovery and Development, Nov. 15–19, 1998, San Francisco, California.

—○— COMPARATIVE PREPARATION
—□— TEST PREPARATION

CYCLOSPORIN-CONTAINING PHARMACEUTICAL COMPOSITION

BACKGROUND OF THE INVENTION

1. Field of the invention

The present invention relates to a pharmaceutical composition containing cyclosporin. More specifically, the present invention relates to a pharmaceutical composition containing cyclosporin, an oil component, a hydrophilic cosurfactant consisting of propylene carbonate or a mixture of propylene carbonate and polyoxyethylene-polyoxypropylene block copolymer, and a surfactant. The composition of the present invention is characterized in that it can be dispersed in an external phase such as water, artificial gastric juice and intestinal juice, etc. to form it self-emulsion with mild stirring and therefore, by appropriately adjusting the constitutional ratio of each component the diameter of particles in the inner phase of the emulsion thus formed can be readily controlled to 100 nm or below.

2. Background Art

Cyclosporin is a high molecular peptide compound (molecular weight 1202) consisting of 11 amino acids and has a potent immunosuppressive activity by inhibition of growth and differentiation of T cells. Therefore, cyclosporin has been used for suppression of immunological rejection of the patients, which may be caused by organ and tissue transplantation, for example, transplantation of kidney, liver, heart, bone marrow, pancreas, skin, cornea, etc. In addition, cyclosporin has also been used for suppression of autoimmune diseases, especially inflammatory diseases such as rheumatoid arthritis.

Cyclosporin has a unique structure in which among 11 amino acids 7 amino acids are in the N-methylated form. In addition, cyclosporin, having a cyclic, symmetric structure, has a very low polarity and therefore, is very slightly soluble in water (0.04 mg/ml $H_2O$, 25° C.). Due to such a low water-solubility of cyclosporin, the bioavailability of cyclosporin is as very low as 30% or less. In addition, the absorption of such insoluble compound may be greatly influenced by bile juice secretion and fat amount in food. In the case of cyclosporin, it has been reported that the difference of absorption between each individual is as very great as about 5–50%.

When cyclosporin is administered, 10 to 27% of the absorbed drug is subjected to the first pass effect in liver and the distribution half-life is 0.7 to 1.7 hour and the excretion half-life is 6.2 to 23.9 hours. Such pharmacokinetic parameters of cyclosporin show a great variation between each individuals depending on secretion of bile juice, condition of patient and kind of transplanted organs. In addition, cyclosporin has a very low therapeutic index and frequently shows renal toxicity as the typical side effect. That is, cyclosporin shows renal side effects such as reduction of glomerular filtration, increase in proximal renal tubular reabsorption, etc. A form of chronic progressive cyclosporin-associated nephrotoxicity is characterized by serial deterioration in renal function and morphologic changes in the kidney. Therefore, in U.S.A. cyclosporin is classified as a group of drugs which should be subjected to a periodic therapeutic drug monitoring (TDM).

Since cyclosporin has such specific properties, that is, a very slight solubility, a low bioavailability and a great variation in absorption between each individual, a great dosage unit and a narrow therapeutic index, and the unstable patient condition to be treated with cyclosporin, it is very difficult to establish the optimum drug dosage regimen for survival of transplanted patient by maintanance of efficient and constant blood concentration which can avoid side effects and rejection. Accordingly, numerous studies have been extensively conducted to develop an improved pharmaceutical formulation. Such study of pharmaceutical formulation has been mainly concentrated on the means which can solubilize cyclosporin. Typical example of such means includes the use of liposome, microsphere, the mixed solvent system consisting of general vegetable oil and surfactant, etc., the formation of powdery composition using adsorption, inclusion complex, solid dispersion, etc., and the other numerous formulations.

The oral preparation containing cyclosporin as the main active ingredient has been commercialized in the form of a solution or soft capsule. Recently, the microemulsion preconcentrate composition containing cyclosporin has also been formulated and commercialized in the form of soft capsule.

The microemulsion has been firstly reported by J. H. Schulman in 1943 and mainly studied as the carrier for cosmetic application. General microemulsion is a thermally stable and optically transparent preparation comprising two or more immiscible systems formed by surfactants and has some advantages that it has very low surface tension and small particle size to show high absorption and permeation properties. However, since the formation of microemulsion requires more surfactant than that used for formation of general emulsion, when the microemulsion is administered or applied for a long period, the mucosal irritation to be caused by each component must be considered. Therefore, in medical field the microemulsion has been utilized only in the field of preparations which is applied to the skin in a short period, for example, preparation for hair, detergent, etc.

According to the optimum water-in-oil microemulsion disclosed in U.S. Ser. No. 818,965, it is described that when the microemulsion is prepared by selecting the surfactant and the cosurfactant which is more hydrophilic than the surfactant, and then adding the surfactant and the oil component to the external phase in which the cosurfactant is dissolved, the transparent microemulsion can be efficiently obtained under more stable and variable conditions. In addition, this patent also reports the microemulsion preconcentrate formulation which is prepared by a method that the very slightly soluble drug is dissolved in hydrophilic cosurfactant such as small chain hydrocarbons and then the oil solution produced by mixing the drug solution as prepared above with oil component and surfactant is added to the external phase to form the microemulsion.

In the case of cyclosporin as the very slightly soluble drug, U.S. Pat. No. 4,388,307 discloses the oral liquid preparation prepared by using oil, surfactant and ethanol as the hydrophilic solvent. This preparation is in the form of microemulsion preconcentrate and therefore, before it is administered per oral, it must be diluted with water. Accordingly, it is very difficult to adapt the subject patient to its administration and to control the accurate dosage and as a result, it is impossible to actually apply to the patient who must receive the cyclosporin therapy during his all life since it is uncomfortable to carry.

In order to improve such disadvantages involved in the liquid preparation, it has been proposed that the microemulsion preconcentrate is formulated in the form of soft capsule. However, in case of the cyclosporin soft capsule containing ethanol as hydrophilic component, this capsule preparation must contain a large amount of ethanol for sufficient solubilization of cyclosporin. However, since ethanol permeates the gelatin shell of the capsule to volatilize even at normal temperature, the content of ethanol is reduced in course of time. As a result, when the capsule preparation is stored at high temperature or at normal temperature for long period, the crystallization of cyclosporin may be caused. Thus, the change in constitutional ratio of the composition caused by the change of ethanol content and the crystallization of cyclosporin result in a great variation in the bioavailability of cyclosporin and therefore, it is impossible to obtain the reliable uniform therapeutic effect. In this condition, in an effort to prevent the volatilization of ethanol from the soft capsule preparations during storage, the soft capsule preparations are packed in a special packaging material, such as aluminum-aluminum blister package. However, such special packaging does not completely prevent the change of ethanol content in course of time. Therefore, this also results in a great variation in bioavailability of cyclosporin and may contribute to the manufacturing price increase.

To improve the above-mentioned disadvantages of the use of ethanol as hydrophilic cosurfactant a method using nonethanol component as hydrophilic cosurfactant has also been proposed. U.S. Pat. No. 5,342,625 discloses the soft capsule preparation formulated from microemulsion concentrate which solves the above-mentioned problems. In this patent, a pharmaceutical composition in the form of microemulsion concentrate in which a pharmaceutically acceptable $C_{1-5}$ alkyl or tetrahydrofurfuryl di- or partial-ether of low molecular mono- or poly-oxy-alkanediol, for example, diethyleneglycol monoethyl ether [e.g. Transcutol] or tetrahydrofurfurylalcohol polyethylene glycol [e.g. Glycofurol], or 1,2-propylene glycol is used as a hydrophilic cosurfactant and ethanol is used as a hydrophilic co-solvent is disclosed. However, all the hydrophilic cosurfactants used in this patent are glycols having the alcoholic group (—OH) in their structure.

Since such —OH group containing glycols are very hygroscopic, they absorb moisture present in atmosphere and further have a high permeability to gelatin shell. Therefore, it is very difficult to formulate the composition containing such glycolic cosurfactant into the soft capsule preparation. Particularly, in encapsulating and drying procedures during the preparation of soft capsules water present in the capsule shell is absorbed into the capsule contents by 20% of the amount of the hygroscopic solvent to cause the change in constitutional ratio of the composition and then in drying procedure water is distributed again into the gelatin shell together with the constituents of the composition and volatilized through the outer capsule shell. According to this, the composition of this patent has disadvantages that the initial constitutional ratio of the composition is greatly changed to cause the change in the appearance of the preparation and also the decrease in production yield.

Furthermore, since the solvent used in the above U.S. patent has it softening effect on gelatin shell, in view of the pharmaceutical formulation this composition also has the problem that the stability of appearance of the gelatin capsule is greatly reduced. Such problem is more serious when the solvent is those used also as the plasticizer for gelatin, for example, propylene glycol or glycerin. For this reason, the use of propylene glycol as the main solvent is almost impossible. Specifically, propylene glycol is used generally by approximately 5% of the capsule contents and may be used by approximately 10% together with a hardening agent for gelatin shell at the most. When the content of propylene glycol is over 10%, the stability of appearance of the gelatin shell is greatly affected.

As one method for improving such disadvantages, Korean Patent Application No. 94-13945 discloses a cyclosporin soft capsule composition (trade name: Neoplanta®) using dimethylisosorbide as a hydrophilic cosurfactant. In this patent, it is described that since dimethylisosorbide used as the hydrophilic solvent has substantially no permeability to the gelatin shell in comparison to the hydrophilic cosurfactants used in the prior art, the soft capsule preparation using dimethylisosorbide provides some advantages that it does not show the change in appearance of the capsule and content of the ingredients.

Dimethylisosorbide is commercialized under trade name Arlasolve® and its chemical name is 1,4:3,6-dianhydro-2, 5-dimethyl-D-glucitol. It is a solvent which has been generally used as a percutaneous absorption promoting agent only in the field of topical pharmaceutical ointment or cosmetics such as lotions.

As mentioned above, the conventional microemulsion composition requires more surfactant than the general emulsion and therefore, in the case of drug which is continuously administered to the patient during his whole life after transplantation, for example, cyclosporin, the toxicity due to long term administration of solvent and surfactant used in the preparation of microemulsion must be considered. In this connection, the $LD_{50}$ value of each surfactant used in cyclosporin formulations in the prior art is as follows: dimethylisosorbide 5.63 ml/kg (rat, per oral), Cremophor RH40>16 g/kg (rat, per oral), Glycofurol 3.5 ml /kg (mouse, intravenous injection) and propylene glycol 21–33.7 g/kg (rat, per oral). In case of the organic solvent of which the toxicity has been relatively well known, the $LD_{50}$ value of each solvent is as follows: acetonitrile 3.8 g/kg (rat, per oral), acetone 10.7 ml/kg (rat, per oral), benzene 3.8 ml/kg (rat, per oral), toluene 7.53 g/kg (rat, per oral), isopropanol 5.8 g/kg (rat, per oral), butanol 4.36 g/kg (rat, per oral), and propylene carbonate, which is used in the present invention as the solvent, 29 g/kg. In considering the $LD_{50}$ values as above, the toxicity of dimethylisosorbide is relatively high as much as the toxicity of general organic solvents and therefore, it is expected that the long term administration of the composition containing dimethylisosorbide per oral may cause some problems. Furthermore, according to this patent dimethylisosorbide is used in an amount 4 times as much as cyclosporin on the basis of weight. This must be seriously considered in view of the fact that this drug is administered to the patient through his whole life.

In addition, in case of the cyclosporin soft capsule composition using dimethylisosorbide, it is disadvantageous that obtain the comparable drug absorption to the commercial product Sandimmun Neoral® and the solubilizing effect sufficient to prevent the precipitation of cyclosporin the solvent is used in a relatively larger amount than the active ingredient. This means an increase in the unit dosage. That is, the hydrophilic cosurfactant, i.e. dimethylisosorbide is used in the 4 times amount per unit weight of cyclosporin. Therefore, the total weight of the unit dosage form of Neoplanta® capsule containing 100 mg of cyclosporin is about 1270 mg which is about 1.2 times as much as the weight of unit dosage form of the prior formulation (Sandimmun Neoral®). In addition, the price of dimethylisosorbide is 20 to 30 times as high as the price of solvents used in the prior art to cause an increase in the manufacturing cost of the preparation and the price of drug.

Thus, the present inventors have studied numerous cyclosporin preparations using various hydrophilic cosurfactants, oils and surfactants in view of their stability and bioavailability to prepare the cyclosporin-containing composition which makes up for various disadvantages involved in the pharmaceutical preparations of the prior art and is suitable for the formulation into the soft capsule and to establish the reliable drug dosage regimen with low toxicity and small dosage unit. As a result, we have identified that when as the hydrophilic cosurfactant in the cyclosporin-containing composition propylene carbonate, which is a pharmaceutically acceptable solvent, or a mixture of propylene carbonate with polyoxyethylene-polyoxypropylene block copolymer in a liquid state at room temperature is used, the above-mentioned requirement can be satisfied and the disadvantages involved in the prior art preparations can also be improved, and thus completed the present invention.

Accordingly, the object of the present invention is to provide a cyclosporin-containing pharmaceutical composition characterized in that it comprises cyclosporin; propylene carbonate or a mixture of propylene carbonate and polyoxyethylene-polyoxypropylene block copolymer as a hydrophilic cosurfactant; an oil component; and a surfactant.

In addition, another object of the present invention is to provide a soft capsule preparation, a hard gelatin capsule preparation sealed with gelatin bending at the conjugated portion or an oral liquid preparation, prepared from the cyclosporin-containing pharmaceutical composition as defined above.

The foregoing has outlined some of the more pertinent objects of the present invention. These objects should be construed to be merely illustrative of some of the more pertinent features and applications of the invention. Many other beneficial results can be obtained by applying the disclosed invention in a different manner or modifying the invention within the scope of the disclosure. Accordingly, other objects and a more thorough understanding of the invention may be had by referring to the disclosure of invention and the drawings, in addition to the scope of the invention defined by the claims.

BRIEF DESCRIPTION OF DRAWINGS

For a thorough understanding of the nature and objects of the invention, reference should be had to the following detailed description taken in connection with the accompanying drawings in which.

DISCLOSURE OF INVENTION

The present invention relates to a cyclosporin-containing pharmaceutical composition characterized in that it comprises cyclosporin; propylene carbonate or a mixture of propylene carbonate and polyoxyethylene-polyoxypropylene block copolymer as a hydrophilic cosurfactant; an oil component; and a surfactant. This composition can improve various problems involved in the prior art as mentioned above when it is formulated in the form of soft capsules.

More specifically, the present invention relates to a pharmaceutical composition containing (1) cyclosporin as an active ingredient, (2) propylene carbonate or a mixture of propylene carbonate and polyoxyethylene-polyoxypropylene block copolymer in a liquid state at room temperature as a hydrophilic cosurfactant, (3) one of medium chain triglyceride and mono- and di-glyceride or a mixture thereof as an oil component, and (4) a surfactant.

The first essential component of the cyclosporin-containing pharmaceutical composition according to the present invention is cyclosporin as an active ingredient. Cyclosporin is a cyclic peptide compound consisting of 11 amino acids and having a pharmacologically useful activity, i.e. immunosuppresive activity. Although cyclosporin A, B, C, D and G depending on the structure of constituent amino acids can be used as the cyclosporin component in the present invention, cyclosporin A is mostly preferred since its pharmacological activity and clinical indication and effectiveness are well established in the art.

The second essential component of the composition of the present invention is a hydrophilic cosurfactant. The hydrophilic cosurfactant which can be used in the cyclosporin-containing pharmaceutical composition of the present invention includes propylene carbonate or a mixture of propylene carbonate and polyoxyethylene-polyoxypropylene block copolymer in a liquid state at room temperature.

As one of the cosurfactant which can be used in the present invention, propylene carbonate is a colorless transparent liquid and has a chemical name (±)-4-methyl-1,3-dioxolan-2-one. It has been used as a solvent for the pharmaceutical preparations for oral and topical administration. The chemical structure of propylene carbonate is represented by the following formula (I):

(1)

Propylene carbonate is a substance which is used as a non-volatile, stable liquid carrier particularly in hard gelatin capsule preparation. In addition, since it has a boiling point of 242° C., it does not volatilize during storage at normal temperature or in preparing the soft capsules at high temperature and therefore, can ensure the stability of the preparation during storage and production procedures. Further, since propylene carbonate does not contain hydroxy group (—OH), it does not have a problem of serious hygroscopic property differently from glycols and also not have a permeability to gelatin capsule shell. Due to the good solubilizing effect of propylene carbonate for very slightly soluble drug it can be readily applied to cyclosporin.

Another substance which can be used together with propylene carbonate as the hydrophilic cosurfactant in the composition of the present invention is polyoxyethylene-polyoxypropylene block copolymer which is liquid at room temperature. Such block copolymer has been commercialized under trade name Pluronic L10, L31, L35, L43, L101, 31R1, Poloxamer 124, etc., with Poloxamer 124 which is pharmaceutically acceptable being preferably used as the mixture with propylene carbonate. Poloxamer 124 is also available under trade name Lutrol or Pluronic L14, Synperonic PE L44, etc. Poloxamer is a hydrophilic, high molecular surfactant having molecular weight of 2000 to 18000 and can be used as solubilizer for medicinal component, lipid emulsion, ointment base, binder or coating agent for tablets, gelling agent, etc. Although poloxamers have different properties depending on their series, they generally are thermally stable with the flashing point of 260° C. and particularly, poloxamer 124 is well dissolved in an organic solvent such as propylene glycol or xylene, contary to other poloxamers. In addition, in comparison with the other solvent used for formulation of cyclosporin in the prior art poloxamer has no hygroscopic property and therefore, does not cause the change in the constitutional ratio due to dissolution of gelatin shell, permeation and evaporation.

As the cosurfactant in the present invention, either propylene carbonate alone or a mixture of propylene carbonate and polyoxyethylene-polyoxypropylene block copolymer in a liquid state at room temperature can be used. When the mixture of propylene carbonate and polyoxyethylene-polyoxypropylene block copolymer in a liquid state at room temperature is used as the hydrophilic copolymer in the present invention, they can be combined in the ratio of 1:0.1–5, preferably 1:0.1–3, more preferably 1:0.1–1, on the basis of weight.

In the cyclosporin-containing pharmaceutical composition according to the present invention, the ratio of the hydrophilic cosurfactant to cyclosporin is preferably in the range of 1:0.5–5, more preferably 1:1–3, on the basis of weight.

The use of the above-defined hydrophilic cosurfactant selected according to the present invention in the cyclosporin-containing preparation can provide a solubilizing effect sufficient for cyclosporin and also provide some advantages that the selected cosurfactant does not cause the change in capsule appearance and the precipitation of active ingredient cyclosporin due to the change in solvent content, reduces the manufacturing cost to provide an economical effect and does not have any toxicity problem of the solvent.

The third essential component contained in the composition of the present invention is an oil component. In the composition of the present invention, any one of medium chain triglyceride and mono- and di-glyceride or a mixture thereof can be used as the oil component.

As the medium chain triglyceride in the oil component a triglyceride of saturated fatty acid having 8 to 10 carbon atoms can be used. The oil in the form of such medium chain triglyceride provides many advantages in comparison to general vegetable oils. Specifically, since the medium chain triglyceride has a low sensitivity to oxidation and a density of 0.94–0.95, which is higher than the density of vegetable oils and near to the density of water, the emulsion using this triglyceride oil component is more stable than the general emulsion. In addition, the medium chain triglyceride has lower hydrophobic property than vegetable oils and its solubilizing effect to the active ingredient is superior to general oil components. Therefore, when the composition is prepared using this medium chain triglyceride, it is possible to obtain higher concentration of the active ingredient without significant increase in the viscosity of the composition. This means that the medium chain triglyceride is an oil very suitable to the drug of which the dose is great such that the concentration of active ingredient to carrier is as high as 10% and which has very low polarity and therefore, is very slightly soluble in water, for example, cyclosporin. Such medium chain triglyceride has been commercialized under trade name Sefol 860, Sefol 870, Sefol 880, Miglyol 810, Miglyol 812, Miglyol 818, etc.

As another oil component, a mono- and di-glyceride can be used. The mono- and di-glyceride is a mixture of glycerol mono- and di-esters of fatty acid in which monoglyceride is contained in the ratio of at least 40%. In order to control the absorption of cyclosporin, it is more preferable that the mono- and di-glyceride contain monoglyceride of $C_{18}$ fatty acid as the main component, which is commercialized under trade name GMO AV1 (Croda Co.), ATMOS 300 (ICI Co.), GMOrphic-80 (Eastman Co.), etc., can be preferably used.

In the composition of the present invention, either any one of the above defined oils singly or a mixture of two or more oils can be used as the oil component. When a mixture of medium chain triglyceride and mono- and di-glyceride is used as the oil component, they are present in the mixing ratio of 1:0.1–1, preferably 1:0.1–0.5, on the basis of weight.

In the cyclosporin-containing pharmaceutical composition of the present invention, the constitutional ratio of the oil component to cyclosporin is preferably 1:0.5–5, more preferably 1:1–3, on the basis of weight.

The fourth essential component in the cyclosporin-containing pharmaceutical composition according to the present invention is a surfactant. As the surfactant in the composition, any pharmaceutically acceptable surfactant can be used, if it is pharmaceutically acceptable, is miscible with the oil component and the hydrophilic cosurfactant component to form an emulsion under mild stirring in the external phase and can adjust the particle diameter in the inner phase to 100 nm or below by controlling the constitutional ratio thereof. The surfactant which can be preferably used for this purpose includes polyoxyethylene glycolated natural or hydrogenated vegetable oils, polyoxyethylene sorbitan fatty acid esters, polyoxyethylene fatty acid esters, polyoxyethylene alkyl ethers, polyethylene glycol mono- and di-fatty acid esters, transesterification product of natural vegetable oil triglyceride with polyalkylene polyol, etc. More preferable surfactant is polyethylene glycol mono- and di-fatty acid esters commercialized under trade name Solutol (BASF), polyoxyethylene sorbitan fatty acid esters commercialized under trade name Tween (Lippo Chem.), the reaction product of castor oil and ethylene oxide commercialized under trade name Cremophor (e.g. Cremophor RH60, RH40, EL, etc., BASF), transesterification product of natural vegetable oil triglyceride and polyalkylene polyol commercialized under trade name Labrafil (e.g. Labrafil M1944 CS, M2125 CS, WL 2609 BS, Labrafac CM-10, Labrasol, Etablissement Gattefosse), etc. Particularly, one or more selected from the group consisting of polyoxyethylene glycolated natural or hydrogenated vegetable oils and transesterification products of natural vegetable oil triglyceride and polyalkylene polyol can be preferably used as the surfactant. If the mixture of polyoxyethylene glycolated natural or hydrogenated vegetable oils and transesterification products of natural vegetable oil triglyceride and polyalkylene polyol is used as the surfactant, they are present in the mixing ratio of 1:0.1–1, preferably 1:0.1–0.5, on the basis of weight.

In the composition of the present invention, either any one of the above defined surfactant alone or a mixture of two or more surfactants can be used as the surfactant. In the cyclosporin-containing pharmaceutical composition of the present invention, the constitutional ratio of the surfactant to cyclosporin is preferably 1:1–7, more preferably 1:3–7, on the basis of weight.

As mentioned above, in the composition of the present invention polyoxyethylene-polyoxypropylene block copolymer which is in a liquid state at room temperature and has an emulsifying property, in combination with propylene carbonate can be used as the hydrophilic cosurfactant. As previously described, it was already disclosed that when the microemulsion is prepared using the surfactant and the cosurfactant having more hydrophilic property than the surfactant, the microemulsion can be produced under various conditions and the microemulsion thus produced has an excellent stability. In view of this, the composition of the present invention uses as the hydrophilic cosurfactant poloxamer 124 which is more hydrophilic surfactant, together with the surfactant component and therefore, can readily form a microemulsion in comparison to the prior preparations using ethanol, propylene glycol, transcutol, glycofurol, dimethylisosorbide, etc. which act merely as the solvent and have practically no emulsifying property. Therefore, the cyclosporin-containing pharmaceutical composition according to the present invention can form a more advantageous and stable microemulsion under the patient's variable gastro-intestinal conditions in comparison to the microemulsion preconcentrate of the prior art.

In the composition according to the present invention, four essential components are present preferably in the ratio of cyclosporin:hydrophilic cosurfactant:surfactant:oil component=1:0.5–5:1–7:0.5–5, and more preferably in the ratio of cyclosporin:hydrophilic cosurfactant:surfactant:oil component=1:1–3:3–7:1–3, on the basis of weight. In addition to this composition, the composition illustrated in the following examples can be mentioned as the further preferable compositions according to the present invention.

The cyclosporin-containing pharmaceutical composition according to the present invention can further contain, if necessary, pharmaceutically acceptable additives as conventionally used. Such additives include, for example, antioxidant (e.g. tocopherol, BHA, etc.), viscosity regulator, releasing regulator, perfume (e.g. peppermint oil, etc.), preservative (e.g. benzylalcohol, parabens, etc.), coloring agent, etc.

For practical use in the clinical field, the composition of the present invention can be formulated into the oral preparations such as soft capsules, hard capsules sealed with gelatin bending at the conjugated portion, oral liquid preparations, etc., using pharmaceutically acceptable additives according to the conventional method in the pharmaceutical field. For example, when the composition of the present invention is formulated into the soft capsule preparation, according to the conventional method for preparing soft capsules it can be prepared, for example, by first dissolving cyclosporin in the hydrophilic cosurfactant under mild warming, adding the oil component and the surfactant to the resulting solution and then uniformly mixing the constituents and then, if necessary, adding the pharmaceutically acceptable additive, and formulating the resulting mixture into the soft capsule by means of a machine for preparing soft capsules.

Particularly, when the composition according to the present invention is formulated into the soft capsule preparation, the soft capsule thus prepared shows a comparable blood level of cyclosporin to the commercial cyclosporin soft capsules and further, does not cause any change of the preparation in course of time due to the volatilization and permeation of the constituents and reduces the toxicity of solvent, which may make a problem in long-term therapy. Accordingly, the composition of the present invention attains an apparent improvement in the relevant technical field.

The present invention will be more specifically illustrated by the following examples. However, it should be understood that the present invention is not limited by these examples in any manner.

EXAMPLE 1

Cyclosporin Capsule for Oral Administration

| Component | Content (mg/500 mg Cap.) |
| --- | --- |
| Cyclosporin | 50.0 |
| Propylene carbonate | 120.0 |
| Cremophor RH40 | 250.0 |
| Miglyol 812 | 80.0 |

50 g of Cyclosporin was dissolved in 120 g of propylene carbonate with stirring and heating. The given amount of oil component and Cremophor RH40 were added to the obtained solution and then stirred until the homogeneous solution is formed. The resulting cyclosporin-containing composition was poured to a machine for preparing soft capsule and then encapsulated according to the conventional method to produce the soft capsule preparations. Each capsule contains 50 mg of cyclosporin. Alternatively, after the cyclosporin-containing composition is prepared as mentioned above, the composition was filled in hard gelatin capsules and the conjugated portion of hard capsules was sealed with a gelatin bending to produce the hard capsules containing 50 mg of cyclosporin per capsule.

EXAMPLE 2

Cyclosporin Soft Capsule for Oral Administration

The soft capsule preparations of Examples 2-A to 2-C having the composition described in the following Table 1 were prepared using propylene carbonate alone or in combination with polyoxyethylene-polyoxypropylene block copolymer which is liquid at room temperature as the hydrophilic cosurfactant according to the same method as Example 1.

TABLE 1

| | Example No. | | |
| --- | --- | --- | --- |
| Constituent | 2-A (mg/Cap.) | 2-B (mg/Cap.) | 2-C (mg/Cap.) |
| Cyclosporin | 50.0 | 50.0 | 50.0 |
| Propylene carbonate | 100.0 | 70.0 | 100.0 |
| Lutrol L44 | | | 25.0 |
| Pluronic L121 | | 45.0 | |
| Cremophor RH40 | 210.0 | | 175.0 |
| Labrafil | 20.0 | 195.0 | 25.0 |
| GMOrphic 80 | 35.0 | 25.0 | 35.0 |
| Sefol 880 | 100.0 | 150.0 | 90.0 |
| Total | 515.0 | 535.0 | 500.0 |

EXAMPLE 3

Cyclosporin Soft Capsule for Oral Administration

The soft capsules of Examples 3-A to 3-C having the composition described in the following Table 2 were prepared using any one of medium chain triglyceride and mono- and di-glyceride or a mixture of them as the oil component according to the same method as Example 1.

TABLE 2

| Constituent | 3-A (mg/Cap.) | 3-B (mg/Cap.) | 3-C (mg/Cap.) |
| --- | --- | --- | --- |
| Cyclosporin | 50.0 | 50.0 | 50.0 |
| Propylene carbonate | 100.0 | 120.0 | 120.0 |
| Synperonic PE L44 | 40.0 | | |
| Cremophor RH40 | 250.0 | 230.0 | 225.0 |
| GMOrphic 80 | 60.0 | 130.0 | |
| Sefol 880 | 100.0 | | 120.0 |
| Total | 600.0 | 530.0 | 515.0 |

EXAMPLE 4
Cyclosporin Soft Capsule for Oral Administration

The soft capsule preparation was prepared with addition of pharmaceutically acceptable additives to the composition of the present invention according to the same method as Example 1.

| Component | Content (mg/Cap.) |
| --- | --- |
| Cyclosporin | 50.0 |
| Propylene carbonate | 120.0 |
| Miglyol 880 | 100.0 |
| Solutol HS15 | 230.0 |
| Tocopherol | 1.5 |
| Total | 501.5 |

EXAMPLE 5
Cyclosporin Solution for Oral Administration

| Component | Content (mg) |
| --- | --- |
| Cyclosporin | 100.0 |
| Propylene carbonate | 250.0 |
| Poloxamer 124 | 50.0 |
| Cremophor RH40 | 400.0 |
| Labrafil | 200.0 |
| Sefol 880 | 200.0 |
| ATMOS 300 | 100.0 |

According to the same method as Example 1, cyclosporin was dissolved and then filled in a suitable container. When this solution is administered, it is diluted with water.

The stability and pharmacological effect of the cyclosporin-containing pharmaceutical composition produced by using propylene carbonate and poloxamer 124 as the hydrophilic cosurfactant according to the present invention were determined according to the following experiments and compared with those of the prior preparations.

Experiment 1

Test for the reactivity of the hydrophilic cosurfactant according to the present invention with the gelatin shell in comparison to the reactivity of the solvents used in the prior art using a thermoanalyzer:

The reactivities of the hydrophilic cosurfactant used according to the present invention and propylene glycol used as the hydrophilic cosurfactant in the prior preparation with the gelatin shell were determined using a thermoanalyzer.

Each of the hydrophilic cosurfactants and mineral oil as the control solvent was filled in the soft gelatin capsule. The filled capsule was stored at room temperature. At regular intervals, the capsules were cut open by a sharp open blade, and the contents were removed by washing with ether and then about 20 mg of gelatin shell was accurately weighed and analyzed. The programed heating rate was 10° C./minute under nitrogen purge from 25 °C. to 300° C.

Figure 1:
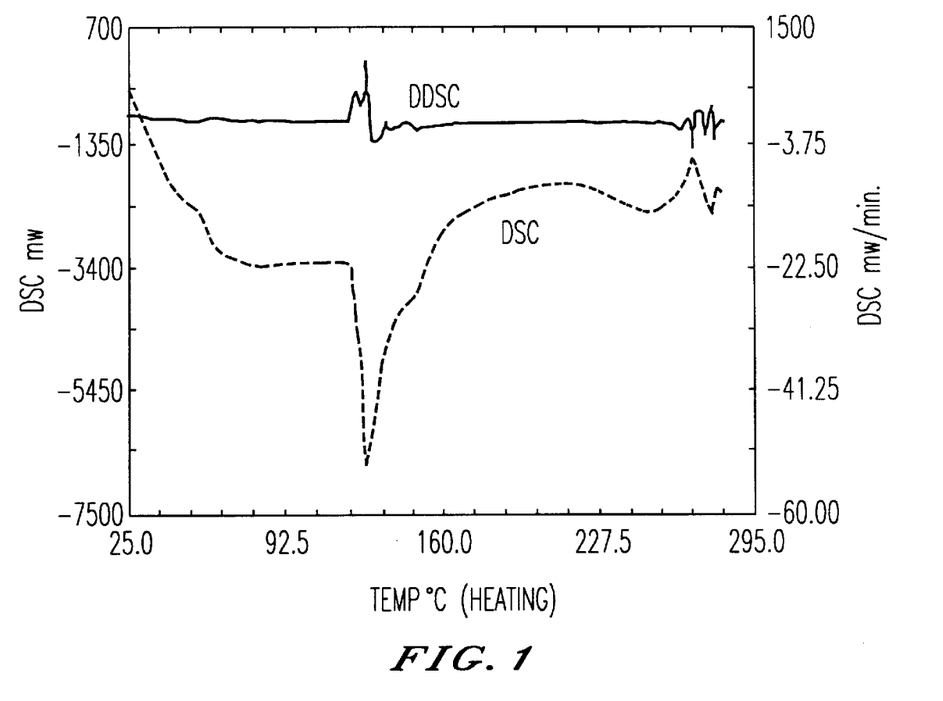
FIG. 1 is a DSC and DDSC graph of the shell of soft gelatin capsule in which mineral oil is filled, after storage for 3 months according to Experiment 1.
Figure 2:
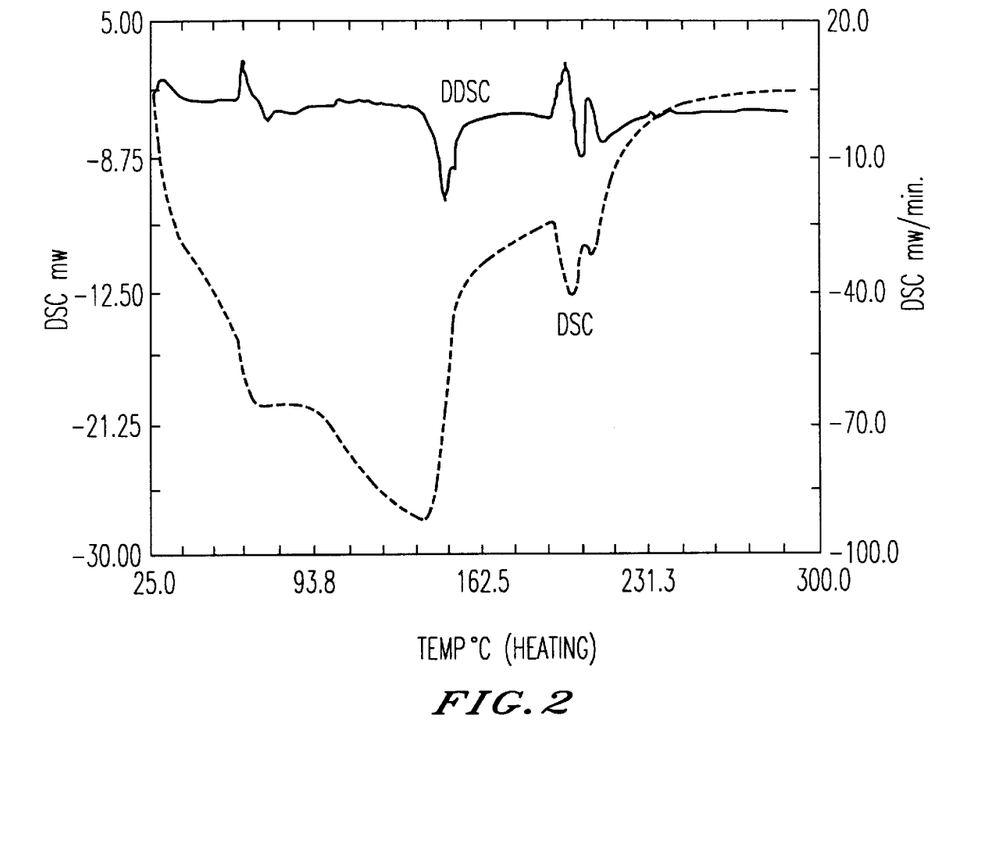
FIG. 2 is a DSC and DDSC graph of the shell of soft gelatin capsule in which propylene glycol is filled, after storage for 3 months according to Experiment 1.
Figure 3:
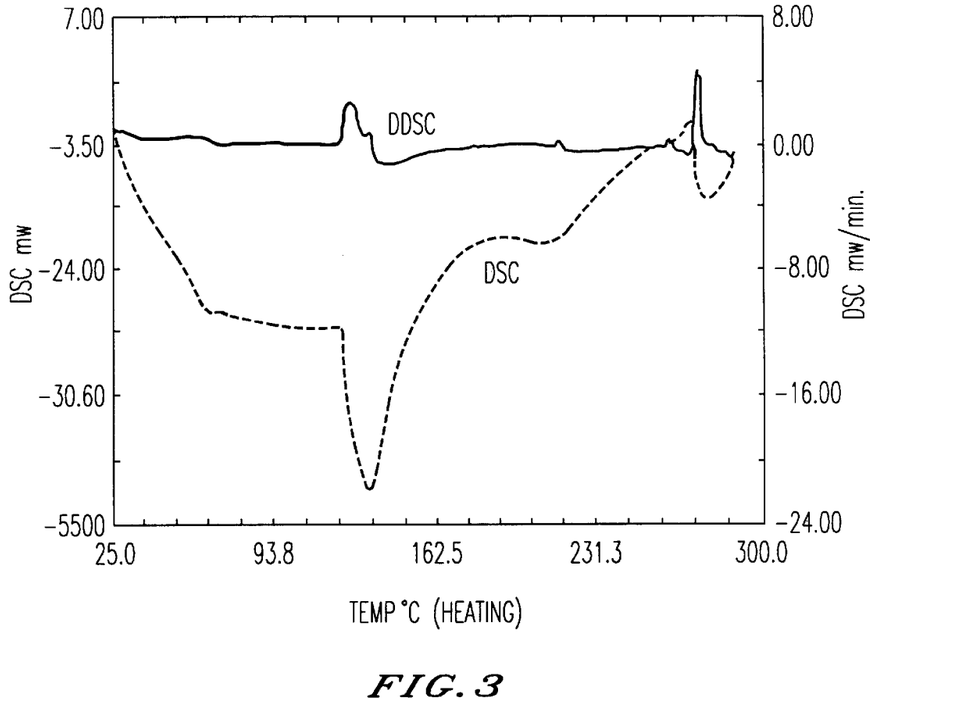
FIG. 3 is a DSC and DDSC graph of the shell of soft gelatin capsule in which propylene carbonate is filled, after storage for 3 months according to Experiment 1.

The variable DSC and DDSC curves depending on temperature were depicted in FIGS. 1 to 3. Upon comparing the result of thermal analysis for each solvent with the DSC result of gelatin shell of the soft capsule filled with mineral oil, it can be seen that propylene glycol shows a new peak from which it can be noted that the reaction of hydrophilic cosurfactant with gelatin shell occurs concurrently with the distribution due to the permeation of hydrophilic cosurfactant to gelatin shell, and its DSC curve is greatly varied between 25° C. and 100° C. However, in the thermal analysis the hydrophilic cosurfactant according to the present invention shows the substantially same pattern as the shell of gelatin capsule filled with mineral oil.

From this result, it can be noted that contrary to the hydrophilic cosurfactant used in the prior art since the hydrophilic cosurfactant used in the present invention does not occur the reaction and distribution with gelatin shell and therefore, does not cause the change in the contents of the composition, it is a solvent suitable for the soft capsule preparation. Therefore, it is apparent that the preparation produced by using such cosurfactant component according to the present invention is better than the prior preparations in view of stability and reliability on the pharmacological effect.

Experiment 2

Change in the constitutional ratio due to volatilization of the solvent in course of time and comparison of the stability of the preparations influenced by such change of the constitutional ratio:

The change in the constitutional ratio of the composition due to volatilization of the hydrophilic component during storage after the soft capsule is prepared, and the stability of the preparation influenced by the change in the constitutional ratio of the composition were determined. In this test, the cyclosporin-containing preparation using propylene carbonate and poloxamer 124 as the hydrophilic cosurfactant according to the present invention was used as the test preparation and the preparation produced by using ethanol as the cosurfactant according to the prior art (Sandimmun Neoral®) was used as the comparative preparation.

The conditions for storage were as follows: Each of the test preparation and the comparative preparation was packed in a bottle or a aluminum foil and each package was stored under three kinds of conditions, i.e. 35° C., relative humidity 75%/35° C., and drying condition/ normal temperature, respectively. Then, the change in the content of ethanol and propylene carbonate in each preparation was measured and compared therewith. For this, the content of propylene carbonate was measured by HPLC and the content of ethanol was measured by GC after pretreatment of the aliquot of the contents of the composition.

The conditions for analysis are as follows:

A) Propylene Carbonate

Apparatus: Waters HPLC system, Mobile phase: water/methanol=9:1(v/v), Flow rate: 1.0 ml/min., Column: Zobax ODS column, Internal standard: resorcinol, Injection volume: 100 μl, Detection wavelength: 190 nm B) Ethanol Pretreatment: Aliquot of the contents of the composition was separated and 30 ml of chloroform was added thereto. The mixture was sonificated for 15 minutes and then 20 ml of chloroform was added and thoroughly mixed.

Analysis: Column: Porapak Q (100–120 mesh, length: 1 m), Column temperature: 135° C., Detector: FID (temperature: 20° C.), Injection temperature: 150° C., Carrier gas: $N_2$ gas (0.65 kg/cm$^2$), air (0.8kg/cm$^2$), Injection volume: 5 μl, Internal standard: diethylether The Lest results as measured are described in the following Tables 4 and 5.

TABLE 4

Change in the content of hydrophilic cosurfactant in the test preparation and the comparative preparation (bottle package)

| Preparation | Storage condition | Change in the content of hydrophilic cosurfactant (mg/Cap.) | | | | |
|---|---|---|---|---|---|---|
| | | 0 | 1 mon. | 2 mon. | 4 mon. | 8 mon. |
| Comparative preparation (ethanol) | 35° C., RH75% | 62.18 | 48.2 | 35.0 | 18.1 | 1.35 |
| | 35° C., drying | | 52.1 | 46.7 | 40.4 | 26.2 |
| | normal temperature | | 59.2 | 57.0 | 54.8 | 48.41 |
| Test preparation (propylene carbonate) | 35° C., RH75% | 102.0 | 99.8 | 97.9 | 97.2 | 96.4 |
| | 35° C., drying | | 101.2 | 100.5 | 99.4 | 97.2 |
| | normal temperature | | 103.0 | 101.2 | 99.5 | 98.5 |

TABLE 5

Change in the content of hydrophilic cosurfactant in the test preparation and the comparative preparation (aluminum foil package)

| Preparation | Storage condition | Change in the content of hydrophilic cosurfactant (mg/Cap.) | | | | |
|---|---|---|---|---|---|---|
| | | 0 | 1 mon. | 2 mon. | 4 mon. | 8 mon. |
| Comparative preparation (ethanol) | 35° C., RH75% | 62.18 | 56.3 | 50.7 | 47.1 | 35.1 |
| | 35° C., drying | | 60.5 | 58.7 | 55.1 | 49.1 |
| | normal temperature | | 61.0 | 59.8 | 58.1 | 56.4 |
| Test preparation (propylene carbonate) | 35° C., RH75% | 102.0 | 101.5 | 100.5 | 98.7 | 99.3 |
| | 35° C., drying | | 100.3 | 101.5 | 99.8 | 98.9 |
| | normal temperature | | 101.8 | 101.4 | 101.5 | 101.3 |

From the results described in the above Tables 4 and 5, it can be noted that in the test preparation the initial concentration of hydrophilic cosurfactant was consistently retained during the test period of 8 months whereas the comparative preparation shows a dramatic decrease in ethanol content even in the case of aluminum foil package. In view of this result, it is apparent that the cyclosporin-containing pharmaceutical composition using propylene carbonate and poloxamer 124 as the hydrophilic cosurfactant, with the exclusion of ethanol, according to the present invention is outstandingly superior to the known ethanol-containing preparation according to the prior art in view of the storage stability of the preparation.

Experiment 3

Propylene glycol which contains —OH group in its molecular structure and therefore has high hygroscopic and hydrophilic properties is distributed in the capsule shell according to the movement of water present in the contents and gelatin capsule during encapsulation and drying procedures and therefore, is permeated to the capsule shell in course of time. According to this, since the constitutional ratio of the contents is greately varied at the early stage, of manufacturing procedures of the capsule preparation, the stability of the preparation cannot be ensured and further the reliable therapeutic effect cannot be obtained. Therefore, depending on what kind of hydrophilic cosurfactant is used in the cyclosporin preparation the stability of the soft capsule preparation is varied. Hereinafter, the permeability to the gelatin shell of the hydrophilic cosurfactant used in the soft capsule according to the present invention was determined and compared with the shell permeability of propylene glycol, transcutol, glycofurol or dimethylisosorbide used as the hydrophilic cosurfactant in the soft capsule according to the prior art. The content of each solvent in each soft capsule preparation was analyzed by gas chromatography and HPLC. In addition, in order to apply the same condition to each preparation each solvent and Cremophor RH40 were mixed in the ratio of 3:7. At regular intervals, the constant amount of the sample was taken and then analyzed. The test results and analytical conditions are described in the following Table 6.

A) Dimethylisosorbide

Column: Ultra 2; Column temperature: 23° C.; Detector: FID; Detector temperature: 270° C.; Injection temperature: 275° C.; Carrier gas: He; Injection volume: 5 μl; Internal standard: octyl alcohol B) Propylene glycol Column: 10% PEG 20M; Column temperature: 160° C.; Detector: FID; Injection temperature: 200° C.; Carrier gas: $N_2$; Injection volume: 1 μl; Internal standard: pentadecanoic acid methyl ester C) Transcutol Column: Ultra 2; Column temperature: 230° C.; Detector: FID; Detector temperature: 270° C.; Injection temperature: 270° C.; Carrier gas: He; Injection volume: 5 μl; Internal standard: pentadecanoic acid methyl ester D) Glycofurol Column: Ultra 2; Column temperature: 230° C.; Detector: FID; Detector temperature: 270° C.; Injection temperature:

270° C.; Carrier gas: He; Injection volume: 5 μl; Internal standard: pentadecanoic acid methyl ester

TABLE 6

Change in the content of hydrophilic cosurfactant in the soft capsule preparations in course of time

| Prepa-rations | Solvent | Change of the content of hydrophilic cosurfactant (wt %, day) | | | | | | |
|---|---|---|---|---|---|---|---|---|
| | | 0 | 5 | 15 | 30 | 60 | 90 | 120 |
| Test preparation | Propylene carbonate | 30.1 | 29.8 | 28.6 | 28.4 | 28.7 | 27.4 | 28.0 |
| Comparative preparation | Dimethyl-isosorbide | 30.0 | 28.2 | 29.1 | 28.7 | 28.0 | 26.6 | 25.8 |
| | Propylene glycol | 29.9 | 21.9 | 22.8 | 21.0 | 22.4 | 21.5 | 19.5 |
| | Transcutol | 30.1 | 22.1 | 23.1 | 21.9 | 22.1 | 21.7 | 20.3 |
| | Glycofurol | 30.0 | 24.4 | 21.0 | 23.5 | 21.0 | 20.7 | 20.4 |

From the result described in the above Table 6, it can be seen that in comparison to the hydrophilic cosurfactant used in the prior art propylene carbonate used as the hydrophilic cosurfactant in the present invention provides at least comparable stability to dimethylisosorbide and is more stable than propylene glycol, transcutol and glycofurol, and therefore, is retained at the initial content.

Accordingly, it is apparent that since propylene carbonate used in the present invention does not cause any change in the constitutional ratio of the composition, the preparation produced by using such cosurfactant component is better than the prior preparations in view of stability and reliability.

Experiment 4

Comparative test for the bioavailability of the composition of the present invention (test preparation) and the composition as prepared and commercialized in the prior art (comparative preparation):

Test Preparation

| Component | Content (mg/Cap.) |
|---|---|
| Cyclosporin | 100.0 |
| Propylene carbonate | 150.0 |
| Poloxamer 124 | 70.0 |
| Cremophor RH40 | 370.0 |
| Sefol 880 | 200.0 |
| Mono-/di-glyceride | 120.0 |
| Tocopherol | 3.0 |
| Total | 1013.0 |

Comparative preparation: Sandimmun Neoral® 100 mg

A) Test Method

Six(6) dogs (male, body weight 11.0–15.0 kg) were used as the test animals and divided into two groups such that each group contains three dogs. The test was conducted in the manner of a crossover test method at intervals of two weeks during which the preparation is not administered. From 18 hours before administration of each of the test and comparative preparations, the test animals were strictly prohibited from taking any food except water. In this test, each dog received the preparation in an amount corresponding to 100 mg as cyclosporin and then 50 ml of water. After 4 hours from administration of the preparation, the test animals were allowed to take the food. Before administration of the preparation the blood for blank test was taken, and then 2 ml of blood was taken from abdominal vein at scheduled intervals after administration of the preparations. The blood thus obtained was stored in a refrigerator at −18° C. and then subjected to RLA.

B) Result

As the result of administration of the test and comparative preparations to 6 dogs according to the above method, the AUC and blood level of cyclosporin for each preparation are described in the following Table 7.

TABLE 7

AUC of the composition of the present invention and the commercial composition after oral administration

| | Comparative preparation | Test preparation |
|---|---|---|
| A | 2489 | 2690 |
| B | 2684 | 2456 |
| C | 2563 | 2538 |
| D | 2304 | 2381 |
| E | 2373 | 2568 |
| F | 2597 | 2630 |
| G | 2488 | 2501 |
| Average | 2499.7 | 2537.7 |

As can be seen from the result described in the above Table 7, the composition of the present invention shows a substantially comparable bioavailability in dogs to the commercial comparative composition containing cyclosporin. Therefore, it is obvious that the preparation according to the present invention can ensure the reliability equivalent to the known commercial preparation in view of therapeutic effect through absorption of the active ingredient and solve the problems involved in the prior preparations.

Experiment 5

Determination of bioequivalence of the preparation according to the present invention (test preparation) to the cyclosporin-containing commercial preparation (comparative preparation) in human subject:

The bioequivalence of the preparation according to the present invention (test preparation) to the cyclosporin-containing commercial preparation (comparative preparation) produced according to the known method after administration to the human subject was determined.

In this test, 20 to 28 years old 24 healthy adult men who did not take general medicine in recent days were included. First, the volunteers were randomly divided into two groups such that each group contains 12 persons, and subjected to a crossover test with 7 days interval. They received an identical meal the evening before dosing and fasted from 12 hours before until 4 hours after drug administration. After 4 hours from administration of the preparation, the standard meal and water were provided. In this test, the soft capsule prepared according to Example 2-C was used as the test preparation and the commercial product Sandimmun Neoral® was used as the comparative preparation.

Figure 4:
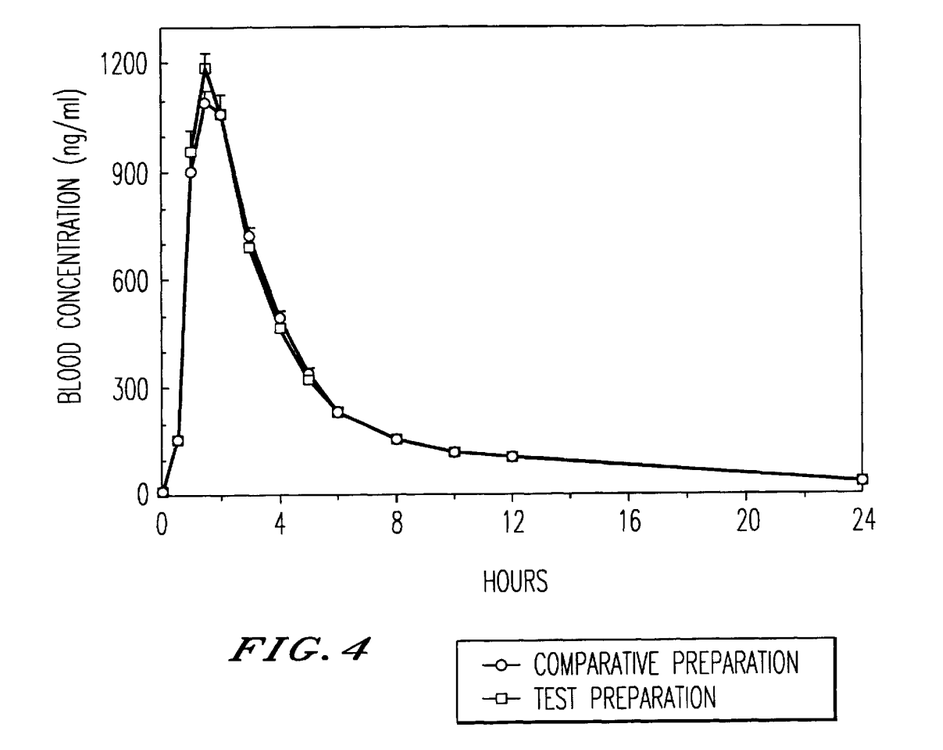
FIG. 4 is a graph showing the cyclosporin level in whole blood after administration of the cyclosporin-containing pharmaceutical composition prepared according to the present invention (test preparation) in comparison with that of the commercial cyclosporin preparation (Sandimmun Neoral®: comparative preparation), in which ⊖ denotes the cyclosporin level in whole blood after administration of the comparative preparation and ⊟ denotes the cyclosporin level in whole blood after administration of the test preparation.

Both of the test preparation and the comparative preparation were administered in an amount of 200 mg as cyclosporin per each person. Venous blood samples for the assay of cyclosporin in whole blood were obtained before closing and at scheduled time intervals. The blood thus obtained was stored in a refrigerator until it is analysed. Concentrations of cyclosporin A were assayed using radioimmunoassay and AUC was calculated according to a trapezoidal method. The bioavailability of each preparation is described in the following Table 8 on the basis of the item for evaluation of bioequivalence and the curve showing blood level of cyclosporin is depicted in FIG. 4.

TABLE 8

Bioavailability of the test preparation of the present invention and the comparative preparation

| Parameters | Comparative preparation (A) | | Test preparation (B) | | P |
| --- | --- | --- | --- | --- | --- |
| | Mean | S.E.* | Mean | S.E. | (B/A)** |
| $AUC_{(0-24\ hr)}$ (ng · hr/ml) | 5379.2 | 194.1 | 5370.2 | 176.2 | 0.99 |
| $C_{max}$ (ng/ml) | 1243.4 | 35.2 | 1208.9 | 28.6 | 0.97 |
| $T_{max}$ (hr.) | 1.6 | 0.1 | 1.6 | 0.1 | 1.0 |

Note)
*S.E.: standard error
**P(B/A): Ratio of average of the test preparation to the average of the comparative preparation As can be shown from Table 8 and FIG. 4, the cyclosporin-containing pharmaceutical composition using propylene carbonate and poloxamer 124 as the hydrophilic cosurfactant according to the present invention shows a substantially equivalent absorption pattern of cyclosporin in comparison to the commercial preparation according to the prior art. In addition, in the test preparation the error level fear blood concentration parameters is reduced in comparison to the comparative preparation. Therefore, it can be assumed that in comparison to the comparative preparation the test preparation can form a better microemulsion in gastro-intestinal tract and is more uniformly absorbed.

From the results of experiments as mentioned above, it is apparent that the cyclosporin-containing pharmaceutical composition according to the present invention can ensure the reliable therapeutic pharmacological effect on at least the same level to the prior preparation and solve the above-mentioned numerous problems involved in the prior preparations.

What is claimed is:

1. A cyclosporin-containing pharmaceutical composition, comprising:
   (1) cyclosporin;
   (2) propylene carbonate;
   (3) Poloxamer 124;
   (4) (i) a medium chain triglyceride, or (ii) a mixture of a mono- and a di-glyceride, or a mixture of (i) and (ii); and
   (5) an additional pharmaceutically acceptable surfactant other than (2) or (3), wherein
       the composition is in the form of a micro emulsion pre-concentrate suitable for oral administration,
       the Poloxamer 124 is a liquid at room temperature, and
       the composition contains (1), the total amount of (2) and (3), (5), and (4), in a weight ratio of 1:0.5–5:1–7:0.5–5.

2. The cyclosporin-containing pharmaceutical composition according to claim 1, wherein (1) is cyclosporin A.

3. The cyclosporin-containing pharmaceutical composition according to claim 1, wherein the composition contains (2) and (3) in a weight ratio of 1:0.1–5.

4. The cyclosporin-containing pharmaceutical composition according to claim 3, wherein the composition contains (2) and (3) in a weight ratio of 1:0.1–1.

5. The cyclosporin-containing pharmaceutical composition according to claim 1, wherein the medium chain triglyceride is a triglyceride of a $C_8$–$C_{10}$ fatty acid.

6. The cyclosporin-containing pharmaceutical composition according to claim 1, wherein the mono- and di- glyceride is a mixture of glycerol mono- and di- esters of a fatty acid.

7. The cyclosporin-containing pharmaceutical composition according to claim 1, (4) is a mixture of medium chain triglyceride and mono- and di- glyceride in a weight ratio of 1:0.1–1.

8. The cyclosporin-containing pharmaceutical composition according to claim 7, wherein (4) is a mixture of medium chain triglyceride and mono- and di- glyceride in a weight ratio of 1:0.1–0.5.

9. The cyclosporin-containing pharmaceutical composition according to claim 1, wherein (5) is selected from the group consisting of polyoxyethylene glycolated natural vegetable oils, polyoxyethylene glycolated hydrogenated vegetable oils, polyethylene glyco mono- and di- fatty acid esters, polyoxyethylene sorbitan fatty acid ethers, polyoxyethylene fatty acid esters, polyoxyethylene alkyl esters, transesterification products of natural vegetable oil triglyceride and polyalkylene polyol, and mixtures thereof.

10. The cyclosporin-containing pharmaceutical composition according to claim 9, wherein (5) is selected from the group consisting of polyoxyethylene glycolated natural or hydrogenated vegetable oils, polyoxyethylene glycolated hydrogenated vegetable oils, and transesterification products of natural vegetable oil triglyceride and polyalkylene polyol.

11. The cyclosporin-containing pharmaceutical composition according to claim 10, wherein (5) is a mixture of polyoxyethylene glycolated natural or hydrogenated vegetable oils and transesterification products of natural vegetable oil triglyceride and polyalkylene polyol, in a weight ratio of 1:0.1–1.

12. The cyclosporin-containing pharmaceutical composition according to claim 11, wherein (5) is a mixture of polyoxyethylene glycolated natural or hydrogenated vegetable oil and transesterification products of natural vegetable oil triglyceride and polyalkylene polyol, in a weight ratio of 1:0.1–0.5.

13. The cyclosporin-containing pharmaceutical composition according to claim 1, wherein the composition contains (1), the total amount of (2) and (3), (5) and (4), in a weight ration of 1:1–3:3–7:1–3.

14. The cyclosporin-containing pharmaceutical composition according to claim 1, further comprising one or more pharmaceutically acceptable additives selected from the group consisting of antioxidants, preservatives, and stabilizers.

15. The cyclosporin-containing pharmaceutical composition according to claim 1, which is in the form of an orally administrable preparation.

16. The cyclosporin-containing pharmaceutical composition according to claim 15, wherein the orally administrable preparation is a soft capsule, a hard capsule sealed with a gelatin bending at the conjugated portion, or an oral liquid preparation.

17. A method of orally administering cyclosporin, comprising administering to a subject the composition of claim 1.

* * * * *